United States Patent [19]

Schunk et al.

[11] 4,201,915
[45] May 6, 1980

[54] PNEUMATIC INFRARED RADIATION DETECTOR HAVING A HERMETICALLY SEALED CHAMBER AND A WINDOW

[75] Inventors: Günter Schunk; Albert Randow, both of Bruchköbel, Fed. Rep. of Germany

[73] Assignee: Leybold-Hereaus GmbH & Co. KG, Cologne, Fed. Rep. of Germany

[21] Appl. No.: 902,617

[22] Filed: May 2, 1978

[30] Foreign Application Priority Data

May 7, 1977 [DE] Fed. Rep. of Germany ........ 2720636

[51] Int. Cl.² ................................................ G01J 1/00
[52] U.S. Cl. ...................................... 250/343; 313/110
[58] Field of Search ................ 250/343, 344, 345, 346; 313/110

[56] References Cited
U.S. PATENT DOCUMENTS

| | | | |
|---|---|---|---|
| 3,781,910 | 12/1973 | Herrmann | 250/343 |
| 3,904,880 | 9/1975 | Benz et al. | 250/343 |
| 4,154,087 | 5/1979 | Schunk et al. | 73/27 R |

OTHER PUBLICATIONS

Turnbull, M.S. "Non-Dispersive Infra-Red Gas Analysers" *Electronics and Instrumentation* (Mar. 1972) vol. 2, No. 12, pp. 11–15.

*Primary Examiner*—Alfred E. Smith
*Assistant Examiner*—Janice A. Howell
*Attorney, Agent, or Firm*—Sprung, Felfe, Horn, Lynch & Kramer

[57] ABSTRACT

A pneumatic infrared radiation detector for intermittent irradiation with infrared light has a hermetically sealed chamber including a metal cup having a highly reflective inner surface forming the back of the chamber and a flange-like rim at the open end thereof. A radiation admitting window is disposed at the open end of the cup and a flow detector is connected to the chamber. The cup comprises a thin-walled noble metal vessel comprising one of gold and silver and the window is composed of at least one of calcium fluoride and barium fluoride and sealed vacuum tight to the cup with glass solder having a coefficient of expansion of between 110 and 150. $10^{-7}$/K.

4 Claims, 2 Drawing Figures

PNEUMATIC INFRARED RADIATION DETECTOR HAVING A HERMETICALLY SEALED CHAMBER AND A WINDOW

BACKGROUND

The invention concerns a pneumatic infrared radiation detector for intermittent exposure to infrared radiation, consisting of a vacuum chamber having a transparent window of materials from the group calcium fluoride and barium fluoride, and having a metal cup with a highly reflective internal surface forming the back of the chamber, and a flange-like margin sealed to the window with a glass solder, plus a housing surrounding the chamber and a current detector connected to the chamber.

Such detectors can be used for a variety of purposes. For example, they can be used in an infrared gas analyzer for the rapid, selective and continuous analysis of gases and vapors. Furthermore, their use as radiation receivers for radiant heat and for the measurement of reflection in the infrared range has been suggested.

It is generally desired, in this connection, that the permeability of the window to radiation extend as far as possible into the long-wavelength range, for the purpose of increasing the spectral sensitivity of the detector. This requirement is the reason for the use of calcium fluoride or barium fluoride as material for the window. Sodium chloride has still more desirable properties in this regard, but its solubility in water precludes its use in practical applications.

The cup forming the back part of the chamber is to be corrosion resistant and is to have a high reflectivity, because the measuring effect is enhanced by the multiple reflection from the bright surfaces. In known detectors the cup consists of a thick-walled body of base metal to the inside of which a thin layer of gold is applied. The joining together of the cup and the window is accomplished in this case by cementing with a synthetic resin. Such a detector, however, does not fulfill all of its requirements: it cannot be degassed by heating it to temperatures above 400° C. Consequently, a chemically or physically acting absorber for the residual gases must be added to the detector. This, however, entails instability of the gas composition, because the binding of the gas to the absorber is, as a rule, temperature-dependent. The detector must furthermore be usable for a great number of common gases, such as carbon monoxide, carbon dioxide, water vapor, sulfur dioxide, nitric oxide, and a great number of hydrocarbons. However, no absorber has yet become known which would be compatible with all of the gases involved. The synthetic resin adhesive, consisting for example of epoxy resin, is sufficiently permeable to water vapor and carbon dioxide to interfere with the application in question.

On account of the known disadvantage of the cementing of the cup and window, attempts have been made to use a glass solder in making the joint. It is obvious that such a glass solder must be one which has the same coefficient of expansion as the material of the window. The coefficient of expansion of calcium fluoride is $235 \cdot 10^{-7}$/K. The coefficient of expansion of barium fluoride is $185 \cdot 10^{-7}$/K. Glass solders having corresponding coefficients of expansion, however, must necessarily have a high content of alkali metal oxides. They are therefore soluble in water and dissolve relatively rapidly in a humid atmosphere. That a detector may be used in a humid atmosphere is not unlikely. Also, water vapor could not be measured with such a detector.

THE INVENTION

The invention, therefore, is addressed to the problem of devising a pneumatic infrared radiation detector of the kind initially described, which can be degassed by heating and can be used for all of the commonly measured gases, and in which a reliable seam will nevertheless be present between the cup and the window.

It has surprisingly been found that the problem stated above can be solved in accordance with the invention by making the cup a thin-walled noble metal vessel (gold, silver), and by using as the glass solder for joining the cup to the window one having a coefficient of expansion between 110 and $150 \cdot 10^{-7}$/K.

Solder glasses as specified above are available commercially with stated coefficients of expansion. The specification, therefore, is sufficient to enable the technical expert to obtain a suitable glass solder. A glass solder particularly suitable for the solution of the stated problem is sold by Schott and Gen. of Mainz under the number 8472. On account of the relatively high coefficient of expansion of the window material, it would have been expected that a glass solder within the range specified by the invention would not be usable under the severe temperature changes involved in the degassing process. It has nevertheless surprisingly been found that the stated problem is completely solvable by the synergistic effect of the combination of the elements of the invention.

Evidently, the fact that the noble metal of the cup is thin is particularly important, since it can therefore more easily follow the thermal expansion of the window without excessive tensions. The thinness of the wall of the cup additionally has the advantage that it can be made of a homogeneous material without resulting in intolerably high acquisition cost. Such a cup can easily be made from the noble metal material in sheet form by pressing or deep drawing. Such a cup has very good reflectivity characteristics and thus results in a high responsiveness in the detector. The solution offered by the invention furthermore permits the use of a cup of much smaller diameter. Whereas it has hitherto been common practice to make such cups with a diameter of, say, 25 mm, the cup diameter in the case of the invention can be 10 mm. This has the advantage that a state of equilibrium can be reached much more rapidly during the pulsed exposure of the detector to the measurement radiation. It has been found that the detector of the invention can be operated at a frequency as high as one kilohertz. Such a high frequency has the advantage that the measurement signals can easily be evaluated by electronic methods, and that the effects of mechanical vibrations on the measuring signal become very slight.

In the device of the invention, the cup can also be joined to the housing in an especially advantageous manner by hard soldering. Afterwards, the bore through which the interior of the cup is to be connected through the flow sensor to an equalization chamber is drilled through this hard solder. The hard soldering advantageously improves the hermetic seal.

BRIEF DESCRIPTION OF THE DRAWINGS

An example of the embodiment of the device of the invention and of its application within an analyzer will now be explained in conjunction with the drawing wherein.

DETAILED DESCRIPTION OF THE INVENTION

Figure 1:
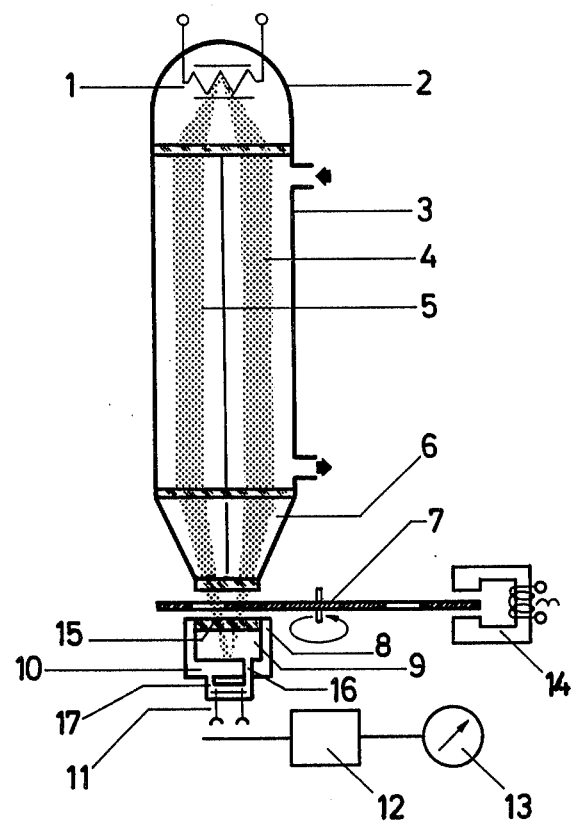
FIG. 1 is a diagrammatic representation of an infrared gas analyzer having a detector as generically described.

In FIG. 1, 1 designates an infrared radiator which is surrounded by a reflector 2. Underneath the infrared radiator is a measuring cell 3 having a measuring side 4 and a comparing side 5. Underneath the measuring cell is a filter cell 6 and a modulating shutter 7. The infrared radiation detector is identified by the number 8, and it consists of an absorption chamber 9 and an equalization chamber 10 which partially surrounds the absorption chamber. The absorption chamber 9 is sealed hermetically on the infrared radiation side by a window 15 permeable to radiation. From the back of the absorption chamber 9 a bore 16 leads to a flow sensing means 11. The space around the flow sensing means 11 is connected by another bore 17 to the equalization chamber 10. The pulsating expansions of the gas in the absorption chamber 9 are therefore communicated to the flow sensing means 11. The modulation shutter 7 causes the rays passing through the measuring side and the comparing side to pass through them alternately. The radiation receiver 8 is sensitized by its special gas charge to the component which is to be measured.

The arrangement shown in FIG. 1 operates in the following manner: if the component for which the measurement is made is absent from the measuring side of the cell, the measuring intensities originating from the two halves of the cell are equal and follow one on the other such that no pressure pulses develop in the receiver. If the component, however, is present, radiation, depending on its concentration, is absorbed in the range of the characteristic absorption band. The intensity coming from the measuring side of the cell, which is absorbed in the receiver, is then attenuated by this amount. Pulsating pressure changes occur, and consequently pulsating equalization currents between the absorption chamber 9 and the equalization chamber 10. The flow sensing means 11 transforms this flow into electrical resistance changes from which the electronic signal processing circuit produces the direct-current reading proportional to the concentration. A flow sensing means which can be used, for example, as the flow sensing means 11, is disclosed, for example, in U.S. Pat. No. 4,154,087. A circuit 12, which need not be described herein, serves for the processing of the signals obtained from the flow sensing means 11 and feeds them to an indicating instrument 13. A regulated eddy current drive 14 provides for a constant rotatory speed of the modulation shutter 7.

Figure 2:
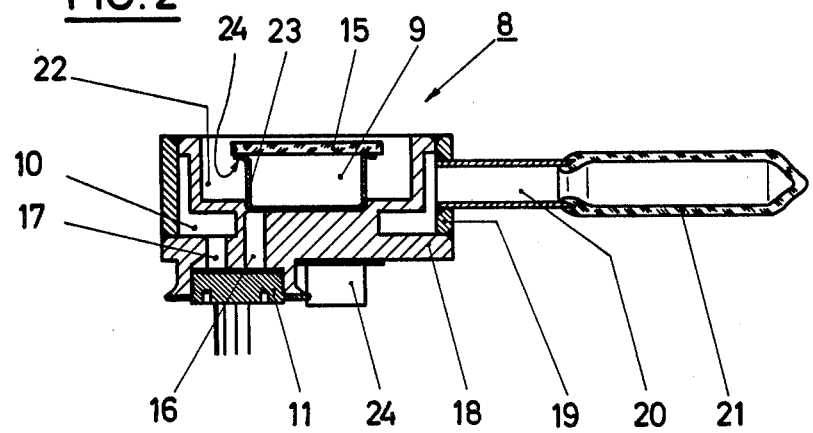
FIG. 2 is a cross-sectional view taken through a detector in which the teaching of the invention has been applied.

In FIG. 2, parts identical to those of FIG. 1 are identified by the same reference numbers. In addition, the following is to be noted: the equalization chamber 10 consists of an annular chamber of L-shaped cross section and is disposed within a housing 18. The equalization chamber 10 is sealed off from the exterior by a collar 19 which is welded hermetically in place and which is penetrated radially by a filler tube 20 whose outer end is closed off by means of a sealed glass tube 21.

The housing 18 has an opening 22 facing upward, in which the absorption chamber 9 is disposed. This consists of a thin-walled cup 23 of sheet gold or silver having a wall thickness of about 0.08 to 0.15 mm and preferably between 0.10 and 0.12 mm. The cup is joined to the housing 18 by hard soldering and a communication is provided between the absorption chamber 9 and the bore 16. The cup 23 has a flange-like rim 24 which is joined to the window 15 by means of the Number 8472 solder glass manufactured by Schott und Genossen. The window consists of calcium fluoride or barium fluoride. Screws 24, of which only one is shown in the drawing, serve to fasten the housing 18 to the rest of the apparatus, which is not represented in FIG. 2.

What is claimed is:

1. In a pneumatic infrared radiation detector for intermittent irradiation with infrared light, of the type having a hermetically sealed chamber including a metal cup having a highly reflective inner surface forming the back of the chamber and having a flange-like rim at the open end thereof and a radiation admitting window at the open end of the cup and a flow detector connected to the chamber, wherein the improvement comprises: the window composed of material selected from the group consisting of calcium fluoride and barium fluoride and sealed vacuum tight to the cup with glass solder having a coefficient of expansion of between 110 and $150.10^{-7}/K$ and the cup comprising a thin-walled noble metal vessel, wherein the noble metal is gold or silver.

2. The detector according to claim 1, wherein the thin-walled cup has a wall thickness of between 0.08 and 0.15 mm.

3. The detector according to claim 2, wherein the wall thickness is between 0.10 and 0.12 mm.

4. The detector according to claim 1, wherein the cup is joined to the housing by a hard solder.

* * * * *